US012018309B2

United States Patent
Farrell et al.

(10) Patent No.: US 12,018,309 B2
(45) Date of Patent: Jun. 25, 2024

(54) OPTIMIZATION OF C-5 STEROL DESATURATION

(71) Applicant: DSM IP ASSETS B.V., Heerlen (NL)

(72) Inventors: Christopher Mark Farrell, Columbia, MD (US); Lisa Ann Laprade, Columbia, MD (US); Otto Martin Lehmann, Kaiseraugst (CH); Joshua Trueheart, Columbia, MD (US); Bastien Jean Wolfgang Chevreux, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 17/051,610

(22) PCT Filed: May 21, 2019

(86) PCT No.: PCT/EP2019/063079
§ 371 (c)(1),
(2) Date: Oct. 29, 2020

(87) PCT Pub. No.: WO2019/224189
PCT Pub. Date: Nov. 28, 2019

(65) Prior Publication Data
US 2021/0222222 A1 Jul. 22, 2021

(30) Foreign Application Priority Data
May 22, 2018 (CH) .................... 00629/18

(51) Int. Cl.
*C12P 33/02* (2006.01)
*C12N 1/16* (2006.01)
*C12N 9/02* (2006.01)
*C12R 1/645* (2006.01)

(52) U.S. Cl.
CPC .............. *C12P 33/02* (2013.01); *C12N 1/165* (2021.05); *C12N 9/0071* (2013.01); *C12R 2001/645* (2021.05)

(58) Field of Classification Search
CPC ....... C12P 33/02; C12N 1/165; C12N 9/0071; C12R 2001/645
USPC ......................................................... 435/61
See application file for complete search history.

(56) References Cited

U.S. PATENT DOCUMENTS

| 7,608,421 B2 | 10/2009 | Lang et al. | |
| 2006/0240508 A1* | 10/2006 | Lang | C12N 9/0071 435/233 |
| 2009/0183270 A1* | 7/2009 | Adams | C12N 15/8274 800/260 |
| 2010/0305341 A1 | 12/2010 | Bailey et al. | |
| 2011/0039299 A1* | 2/2011 | Bailey | C12N 15/52 435/254.2 |
| 2016/0313302 A1 | 10/2016 | Debrabander et al. | |

FOREIGN PATENT DOCUMENTS

| WO | 03/064650 | 8/2003 |
| WO | 2011/067144 | 6/2011 |
| WO | 2017/108799 | 6/2017 |

OTHER PUBLICATIONS

Schutter et al., Genome sequence of the recombinant protein production host Pichia pastoris, Nature Biotechnology, vol. 27, No. 6, (Jun. 2009), pp. 561-566.*
Sequence comparison between Seq Id No. 1 and P. pastoris GS115, UniProt, Result 2, May 4, 2022.*
Love et al., Comparative genomics and transcriptomics of Pichia pastoris, BMC Genomics, (2016), 17:550, pp. 1-17.*
ABSS, sequence comparison between Seq ID No. 14 and U. maydis ERG2 gene, UniProt, Result 1, Feb. 8, 2024.*
Keon et al., Isolation of the ERG2 gene, encoding sterol Δ8→Δ7 isomerase, from the rice blast fungus Magnaporthe grisea and its expression in the maize smut pathogen Ustilago maydis, Curr Genet, vol. 25, (1994), pp. 531-537.*
Rice et al., "EMBOSS: The European Molecular Biology Open Software Suite", The European Molecular Biology Open Software Suite, Trends in Genetics, Jun. 2000, vol. 16, No. 6, pp. 276-277 (2 total pages).
International Search Report for PCT/EP2019/063079 dated Aug. 22, 2019, 5 pages.
Written Opinion of the ISA for PCT/EP2019/063079 dated Aug. 22, 2019, 6 pages.
Sambroook, "Molecular Cloning, a Laboratory Manual", Second Edition, 1989, table of contents (30 total pages).
Ausubel et al., "Current Protocols in Molecular Biology", Nov. 1988, table of contents (3 total pages).
Needleman et al., "A General Method Applicable to the Search for Similarities in the Amino Acid Sequence of Two Proteins", Journal of Molecular Biology, Mar. 28, 1970, vol. 48, No. 3, pp. 443-453 (11 total pages).
Sugawara, T., et al., " Molecular Cloning and Structural Analysis of Human Sterol C5 Desaturase," Biochimica et Biophysica Acta, 1533 (2001), pp. 277-284.
Unknown, Database UniProtKB—C4Qy87, SubName: Full=C-5 sterol desaturase, catalyzes the introduction of a C-5(6) double bond into episterol {ECO:0000313|EMBL:CAY68210.1}, 2 pages, accessed on Jul. 7, 2009.

(Continued)

*Primary Examiner* — Jennifer M. H. Tichy
(74) *Attorney, Agent, or Firm* — Nixon & Vanderhye, PC

(57) ABSTRACT

The present invention is related to an improved method for production of 7-dehydrocholesterol (7-DHC), an important intermediate towards biotechnological production of vitamin D3 or derivatives/metabolites thereof. The invention features modified host strains expressing enzymes having improved C-5 sterol 5 desaturase activity and their use in a process for production of vitamin D3 or derivatives and/or metabolites thereof.

13 Claims, No Drawings
Specification includes a Sequence Listing.

(56) References Cited

OTHER PUBLICATIONS

Zhang et al., Effects of Post-squalene Genes on the Synthesis of 7-Dehydrochlesterol in the Artificial *Saccharomyces cerevisiae*; *China Biotechnology* 36(6) 39-50 (2016).

Unknown, C-5 sterol desaturase, catalyzes the introduction of a C-5(6) double bond in episterol {Komagataella phaffii GS115}; NCBI Reference Sequence XP_002490491; GenPept PLN Oct. 11, 2017.

Unknown, Database UniProtKB—C4Qy87, SubName: Full=C-5 sterol desaturase, catalyzes the introduction of a C-5(6) double bond into episterol {ECO:0000313|EMBL:CAY68210.1}; 2 pages, Jun. 28, 2023, entry version 67.

\* cited by examiner

OPTIMIZATION OF C-5 STEROL DESATURATION

CROSS-REFERENCE TO RELATED APPLICATIONS

This application is the U.S. national phase of International Application No. PCT/EP2019/063079 filed May 21, 2019 which designated the U.S. and claims priority to CH 00629/18 filed May 22, 2018, the entire contents of each of which are hereby incorporated by reference.

REFERENCE TO SEQUENCE LISTING SUBMITTED ELECTRONICALLY

The content of the electronically submitted sequence listing (Name: 4662-4077_Sequence_Listing.txt; Size: 26 kilobytes) filed with the application is incorporated herein by reference in its entirety.

The present invention is related to an improved method for production of 7-dehydrocholesterol (7-DHC), an important intermediate towards biotechnological production of vitamin D3 or derivatives/metabolites thereof. The invention features modified host strains expressing enzymes having improved C-5 sterol desaturase activity and their use in a process for production of vitamin D3 or derivatives and/or metabolites thereof.

Vitamin D3 (also known as cholecalciferol or calciol) can be synthesized in the skin of mammals from provitamin D3 (also known as 7-dehydrocholesterol or 7-DHC) which is the product of cholesterol biosynthesis upon exposure to UV light, whereby 7-DHC is photochemically converted into provitamin D3, which isomerizes at body temperature to the biologically active form vitamin D3. In the liver, vitamin D3 is converted to the biologically inactive 25-hydroxyvitamin D3 (also known as calcidiol, calcifediol, 25-hydroxycholecalciferol, 25-OH-D3 or HyD), which is the major circulating form of vitamin D3. Further hydroxylation occurs in the kidney.

For industrial production of vitamin D3, both chemical and biotechnological synthesis is (in principle) available. Chemical synthesis starts with cholesterol isolated from e.g. wool fat which is dehydrogenated into 7-DHC, an important intermediate in both chemical and biotechnological synthesis. Through exposure by UV-light and further purification/extraction steps 7-DHC is converted into vitamin D3. Modified yeast stains can be used for biosynthesis of 7-DHC, wherein acetyl-CoA is converted in a multi-step enzymatic process into 7-DHC. Said enzymatic conversion takes place in the endoplasmatic reticulum of the yeast. Excessive amounts of sterols, including 7-DHC and precursors thereof, not required in cellular membranes, are toxic to the yeast and are thus stored as steryl esters into intracellular organelles (so-called lipid bodies) from which they can be further isolated. The equilibrium between free sterols and those stored in the lipid bodies (mainly in the form of steryl esters) is triggered via the action of several proteins (enzymes), including action of sterol acyltransferases.

Due to the unspecific action of said sterol acyltransferase enzymes, the steryl ester pool which is stored within the lipid bodies is relatively diverse, including but not limited to e.g. esters of ergosterol, zymosterol, lanosterol, lathosterol, cholesta-5,7,24(25)-trienol, cholesta-8-enol, or 7-DHC. Only 7-DHC can be further processed into vitamin D3.

Thus, it is an ongoing task to generate host cells, such as yeast capable of producing sterols, with high productivity/specificity for 7-DHC and/or reduced accumulation of side-products/intermediates including zymosterol, lanosterol or lathosterol, in particular esters of such intermediates stored in the lipid bodies.

Surprisingly, we now found that the productivity of 7-DHC in a host cell, in particular the ratio of 7-DHC to cholesta-7-enol and/or lathosterol, can be shifted towards 7-DHC via modification of C-5 sterol desaturase activity within the host cell, i.e. expression of heterologous enzymes having C-5 sterol desaturase activity, which leads to higher productivity of the host cell towards 7-DHC as important intermediate in vitamin D3 production.

Thus, the present invention is directed to the use of an enzyme having C-5 sterol desaturase activity in a process for production of 7-DHC, said polypeptide having at least 45%, such as e.g. at least 50, 52, 60, 70, 80, 90, 92, 95, 98 or up to 100% identity to SEQ ID NO:2 being (heterologous) expressed in a suitable host cell for production of 7-DHC, wherein the ratio of 7-DHC to side-products including lanosterol and/or lathosterol is increased by at least 5% compared to a non-modified host cell.

The polypeptide according to SEQ ID NO:2, showing C-5 sterol desaturase activity, including polynucleotides encoding said polypeptide, has been isolated from *Pichia pastoris*.

The terms "C-5 sterol desaturase", "enzyme having C-5 sterol desaturase", "desaturase" or "ERG3-homolog" are used interchangeably herein and refer to enzymes which are capable of catalyzing the conversion of cholesta-8-enol into cholesta-7,24-dienol and/or cholesta-7-enol into cholesta-5,7,24-trienol and/or 7-DHC. The enzymes defined herein are homologs of the *Saccharomyces cerevisiae* ERG3 (SEQ ID NO:8), including polypeptides encoding such polypeptide.

The terms "conversion", "enzymatic conversion", or "desaturation" in connection with enzymatic catalysis of e.g. cholesta-7-enol to 7-DHC and/or cholesta-7,24-dienol to cholesta-5,7,24-trienol are used interchangeably herein and refer to the action of C-5 sterol desaturase as defined herein and known in the art.

The desaturase might be used in an isolated form (e.g. in a cell-free system) or might be introduced and expressed as heterologous enzyme or extra-copies of endogenous enzymes in a suitable host cell. Thus, a suitable host cell, expresses one, two or more copies of desaturase enzymes as defined herein, leading to an increase in 7-DHC and/or improved ratio of 7-DHC compared to cholesta-7-enol and/or lanosterol, said host cell being referred to herein as genetically modified host cell. A genetically non-modified or non-modified host cell as referred herein is the respective host cell carrying only the endogenous C-5 sterol desaturase activity expressed by the endogenous ERG3 gene.

As used herein, the terms "zymosterol", "lanosterol", "lathosterol", "cholesta-5,8,24(25)-trienol", "cholesta-5,7,24(25)-trienol", or "7-DHC" specifying vitamin D3 intermediates include both the free form and the ester form of said compounds. As used herein, a sterol mix contains 7-DHC and "side-products" or intermediates, including but not limited to zymosterol, lanosterol, lathosterol, cholesta-8-enol, cholesta-5,8,24(25)-trienol, or cholesta-5,7,24(25)-trienol.

As used herein, a "cholesterol-producing yeast" cannot produce ergosterol anymore but cholesterol products, including, but not limited to cholesta-5,7,24(25)-trienol, cholesta-5,8,24(25)-trienol, cholesta-7,24(25)-dienol, cholesta-8-enol, 7-DHC or zymosterol. Particularly, this might be achieved via introduction of erg5erg6 double-knock out.

Suitable desaturases as defined herein might be obtainable from different sources, such as e.g. plants, animals, including humans, algae, fungi, including yeast, or bacteria, preferably from fungi, particularly selected from the group consisting of *Saccharomyces, Yarrowia, Klyveromyces, Schizosaccharomyces, Pichia, Candida, Penicillium, Aspergillus, Cryptococcus*, Magneporte, Metarhizium, and *Ustilago*, more preferably selected from *S. cerevisiae, Y. lipolytica, K. lactis, Schizosaccharomyces pombe, P. pastoris, C. albicans, P. roqueforti, A. nidulans, C. neoformans* or *U. maydis*, most preferably from *Pichia pastoris*.

In a preferred embodiment, the enzyme having C-5 sterol desaturase activity is obtainable from *Pichia*, particularly *Pichia pastoris*, such as e.g. a protein encoded by a polynucleotide according to SEQ ID NO:1, more preferably said protein is a polypeptide according to SEQ ID NO:2.

In a further embodiment, the enzyme having C-5 sterol desaturase activity is obtainable from *Penicillium*, particularly *Penicillium* roqueforti, such as e.g. a protein encoded by a polynucleotide according to SEQ ID NO:3, more preferably said protein is a polypeptide according to SEQ ID NO:4.

In one embodiment, the enzyme having C-5 sterol desaturase activity is obtainable from *Schizosaccharomyces*, particularly *Schizosaccharomyces pombe*, such as e.g. a protein encoded by a polynucleotide according to SEQ ID NO:5, more preferably said protein is a polypeptide according to SEQ ID NO:6.

In another embodiment, the enzyme having C-5 sterol desaturase activity is obtainable from *Saccharomyces*, particularly *Saccharomyces cerevisiae*, such as e.g. a protein encoded by a polynucleotide according to SEQ ID NO:7, more preferably said protein is a polypeptide according to SEQ ID NO:8 which is derived from UniProtKB P32352, said enzyme being expressed additionally and/or as replacement of the endogenous ERG3 when using *S. cerevisiae* as host.

Based on the sequences as disclosed herein and on the improved accumulation of 7-DHC and/or reduction of cholesta-7-enol and/or lathosterol in the sterol mix, i.e. leading to at least 84%, such as e.g. 85, 90, 92, 95, 97 or even 100% 7-DHC present in the sterol mix, one could easily deduce further suitable genes encoding polypeptides having C-5 sterol desaturase activity as defined herein which could be used for the desaturation of C-5 sterols as defined herein, particularly cholesta-7-enol and cholesta-7,24-dienol. Thus, the present invention is directed to a method for identification of novel desaturases, wherein a polypeptide with at least 44%, such as e.g. at least 48, 50, 52, 60, 70, 80, 90, 92, 95, 98 or up to 100% identity to the polypeptide according to SEQ ID NO:8, is used as a probe in a screening process for new C-5 sterol desaturases, with preference for production of 7-DHC over cholesta-7-enol and/or lathosterol, leading to at least about 84% 7-DHC in the sterol mix produced by a suitable host strain. Any polypeptide having C-5 sterol desaturase activity and disclosed herein might be used for production of 7-DHC, as long as the desaturase action results in at least about 84% 7-DHC in the sterol mix, based on the total amount of produced sterols and/or increased ratio of 7-DHC to cholesta-7-enol and/or lathosterol.

The present invention is particularly directed to the use of such novel desaturase enzymes, particularly heterologous enzymes, in a process for production of 7-DHC, wherein the production of side-products in the sterol mix including cholesta-7-enol, zymosterol, cholesta-8-enol, or lathosterol is reduced to about 16% or less, such as 15, 12, 10, 8, 5, 3 or less based on the total amounts of sterols, by the action of said desaturases, as defined herein, particularly wherein the percentage of cholesta-7-enol and/or lathosterol towards the amount of 7-DHC is reduced. The process might be performed with a suitable cholesterol-producing yeast cell expressing said heterologous desaturases, preferably wherein the genes encoding said enzymes are heterologous expressed, i.e. introduced into said host cells. 7-DHC can be further converted into vitamin D3 by the action of (known) suitable chemical or biotechnological mechanisms. Increasing the copy-number of ERG3-homologs to more than 1 to be expressed in the host cell, the percentage of side-products can be even further reduced.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person is aware of the fact that plant-derived enzymes might contain a chloroplast targeting signal which is to be cleaved via specific enzymes, such as e.g. chloroplast processing enzymes (CPEs).

The ERG3 enzymes/homologs, as defined herein also encompass enzymes carrying amino acid substitution(s) which do not alter enzyme activity, i.e. which show the same properties with respect to the wild-type enzyme and catalyze the desaturation of C-5 sterols, leading to a percentage of at least about 84% 7-DHC (with reduction of cholesta-7-enol and/or lathosterol towards 7-DHC) in the sterol mix. Such mutations are also called "silent mutations", which do not alter the (enzymatic) activity of the enzymes as described herein.

Depending on the host cell the polynucleotides as defined herein involved in C-5 sterol desaturation might be optimized for expression in the respective host cell. The skilled person knows how to generate such modified polynucleotides. It is understood that the polynucleotides as defined herein also encompass such host-optimized nucleic acid molecules as long as they still express the polypeptide with the respective activities as defined herein. Examples of such host-optimized ERG3 homologs are shown in e.g. SEQ ID NOs:9, 10, and 11.

Thus, in one embodiment, the present invention is directed to a host cell comprising polynucleotides encoding (heterologous) ERG3 homologs as defined herein which are optimized for expression in said host cell, with no impact on growth or expression pattern of the host cell or the enzymes. Particularly, the yeast, e-g. cholesterol-producing yeast cell, is selected from *Saccharomyces*, such as e.g. *Saccharomyces cerevisiae*, wherein one, two or more copies of the polynucleotides encoding the ERG3 enzymes as defined herein are selected from polynucleotides with at least 53%, such as e.g. at least 58, 60, 70, 80, 90, 92, 95, 98 or up to 100% identity to SEQ ID NO:9, including e.g. polypeptides according to SEQ ID NO:9, 10 or 11.

A nucleic acid molecule according to the invention may comprise only a portion or a fragment of the nucleic acid sequence provided by the present invention, such as for instance the sequences shown in SEQ ID NO:1, 3, 5, 7, 9, 10 or 11, for example a fragment which may be used as a probe or primer or a fragment encoding a portion of ERG3 homolog as defined herein. The probe/primer typically comprises substantially purified oligonucleotides which typically comprise a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence according to SEQ ID NO:1, 3, 5, 7, 9, 10 or 11 or fragments or derivatives thereof.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 nnM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The present invention is particularly directed to the use of heterologous enzymes having C-5 sterol desaturase activity as defined herein in a process for production of 7-DHC, an intermediate for vitamin D3. Preferably, the modified enzymes of the present invention are introduced and/or expressed in a suitable host cell, such as yeast, in particular a cholesterol-producing yeast cell, such as selected from *Saccharomyces cerevisiae, Schizosaccharomyces* spp., *Pichia* spp., *Klyuveromyces* spp., *Hansenula* spp. or *Yarrowia lipolytica*, preferably *S. cerevisiae*. The modified host is used for production of 7-DHC, which might be further converted into vitamin D3 and/or 25-hydroxyvitamin D3.

A suitable host cell might be further modified to further increase production of 7-DHC, an important intermediate towards biosynthesis of vitamin D3, and/or reduce accumulation of side-products.

Thus, in one embodiment the invention is directed to a yeast strain having modified C-5 sterol desaturase activity and furthermore wherein ERG5 and ERG6 are inactivated. The yeast cell might be further modified via expression of a heterologous enzyme having C24-reductase activity, particularly selected from EC 1.3.1.72, such as a heterologous C24-reductase that is active on cholesta-7,24-dienol, zymosterol, or trienol (e.g. cholesta-5,7,25-trienol), preferably a plant or vertebrate sterol Δ24-reductase, more preferably from vertebrate source, even more preferably from human, pig, dog, mouse, rat, horse, *Danio rerio* or any known source, as long as it can be expressed within said yeast cell. Most preferably, the sterol Δ24-reductase is selected from *Danio rerio*, rat or human. The sequences expressing said sterol Δ24-reductase enzymes are publicly available, including but not limited to UniProtKB/Swiss-Prot reference Q15392, Q60HC5, Q8VCH6, Q5BQE6, Q39085 or P93472 (see e.g. WO2003064650).

In another embodiment, the host cell according to the present invention might be further modified via introduction of homologs of endogenous enzymes involved in biosynthesis of 7-DHC, such as e.g. C8-sterol isomerase (ERG2), resulting in increased specificity and/or productivity of 7-DHC with reduced accumulation of side-products or vitamin D3 intermediates, including but not limited to zymosterol, lanosterol and/or lathosterol. Preferably, the modified host cell as defined herein comprises a heterologous ERG2, wherein the ERG2 is preferably selected from *Ustilago maydis* (such as e.g. a polypeptide derived from UniProtKB P32360).

In a further embodiment, the host cell according to the present invention might be further modified in the sterol acyltransferase activity, particularly activity of sterol acyltransferase isoform Are1p and/or Are2p, comprising one of more amino acid substitution(s) at (a) position(s) corresponding to residues selected from 592 and/or 595 in the polypeptide according to SEQ ID NO:12.

Thus, the present invention relates in a particular embodiment to a modified yeast strain to be used in a process for production of sterols, particularly 7-DHC, wherein ERG5 and ERG6 are inactivated, optionally expressing a heterologous enzyme having C24-reductase activity as defined herein, and expressing an ERG3 homolog as described herein. Using such a yeast strain, the percentage of 7-DHC present in the sterol mix is in the range of about 84% or more, preferably such as 85, 90, 92, 95, 97 or even 100% based on the total amount of sterols.

In a particular embodiment, the invention relates to a process for improving a yeast cell towards production of 7-DHC, wherein a modified host cell as defined herein, i.e. expressing an ERG3 homolog as defined herein, e.g. via introduction of one, two or more copies of desaturase enzymes as defined herein, in particular cholesterol-producing yeast cell, preferably a yeast cell in which ERG5 and ERG6 are inactivated and wherein optionally a heterologous enzyme having C-24-reductase activity as defined herein is expressed and/or wherein ARE1 and/or ARE2 are modified as described herein and/or wherein optionally homologs of ERG2 are expressed, wherein the host cell is improved such that the percentage of 7-DHC in the total amount of sterol produced by said host cell is increased to at least about 84%, in particular wherein the ratio of 7-DHC to side-products including cholesta-8-enol is increased by at least 2% and as compared to a non-modified yeast strain as defined herein, i.e. expressing only the wild-type (endogenous) ERG3 activity.

In a particular embodiment, the invention relates to a process for improving a yeast cell towards production of 7-DHC, wherein in particular a cholesterol-producing yeast cell, such as a yeast cell in which ERG5 and ERG6 are inactivated and wherein optionally a heterologous enzyme having C-24-reductase activity as defined herein is expressed, said yeast cell expressing an ERG3 homolog as defined herein, e.g. via introduction of one, two or more copies of desaturase enzymes as defined herein, wherein the yeast cell is improved such that the percentage of 7-DHC, in the total amount of sterol produced by said yeast is increased from about 81% or less to at least about 84%, such as e.g. 85, 90, 92, 95, 97 or even 100%, and the percentage of side-products in the sterol mix including cholesta-7-enol, lathosterol and/or cholesta-8-enol and/or zymosterol, is reduced to about 16% or less based on the total amounts of sterols, i.e. a reduction of cholesta-7-enol, lathosterol and/or cholesta-8-enol and/or zymosterol in the range of at least about 16% based on the total amounts of sterols and compared to a non-modified yeast strain expressing the wild-type (endogenous) ERG3 activity.

In one embodiment, the present invention is directed to a process for production of a sterol mix comprising 7-DHC and a mix of cholesta-7-enol (lathosterol) and/or lanosterol in a cholesterol-producing yeast cell, wherein the percentage of 7-DHC is increased by at least about 2%, such as e.g., 3, 4, 5, 10, 15, 20, 30, 40% compared to the percentage of lano-/lathosterol based on the total amount of sterols, said cholesterol-producing yeast cell expressing a (heterologous) desaturase as defined herein, i.e. a polypeptide with least 45%, such as e.g. at least 50, 52, 60, 70, 80, 90, 92, 95, 98 or up to 100% identity to SEQ ID NO:2, more preferably expressed by the respective codon-optimized polynucleotides as defined herein, such as preferably obtainable from *Pichia pastoris*, *Penicillium roqueforti*, or *Schizosaccharomyces pombe*, or *Saccharomyces cerevisiae*, particularly from *Pichia pastoris*.

In one embodiment, the present invention is directed to a process for production of a sterol mix comprising 7-DHC and cholesta-8-enol in a cholesterol-producing yeast cell, wherein the ratio of 7-DHC to cholesta-8-enol based on the total amount of sterols is increased by at least about 2% such as e.g. such as e.g. 3, 4, 5 or at least about 10%, said cholesterol-producing yeast cell expressing a (heterologous) desaturase as defined herein, i.e. a polypeptide with at least about 45%, such as e.g. at least 50, 52, 60, 70, 80, 90, 92, 95, 98 or up to 100% identity to SEQ ID NO:2, more preferably expressed by the respective codon-optimized polynucleotides as defined herein, such as preferably obtainable from *Pichia pastoris*.

In one embodiment, the present invention is directed to a process for production of a sterol mix comprising 7-DHC and zymosterol in a cholesterol-producing yeast cell, wherein the percentage of 7-DHC is increased by at least about 2% such as e.g. 3, 4, 5 or at least about 10% compared to the percentage of zymosterol based on the total amount of sterols, said cholesterol-producing yeast cell expressing a (heterologous) desaturase as defined herein, i.e. a polypeptide with least 45%, such as e.g. at least 50, 52, 60, 70, 80, 90, 92, 95, 98 or up to 100% identity to SEQ ID NO:2, more preferably expressed by the respective codon-optimized polynucleotides as defined herein, such as preferably obtainable from *Pichia pastoris*.

In a particular embodiment, the present invention is directed to a process for production of a sterol mix comprising 7-DHC, zymosterol, cholesta-8-enol, lanosterol and/or lathosterol in a cholesterol-producing yeast cell, wherein the percentage of 7-DHC is increased by at least about 2% such as e.g. 4, 5, 7, 10, 15% or more compared to percentage of said side-products in the sterol mix, said cholesterol-producing yeast cell expressing a heterologous desaturase as defined herein, i.e. a polypeptide with least about 45%, such as e.g. at least 50, 52, 60, 70, 80, 90, 92, 95, 98 or up to 100% identity to SEQ ID NO:2, more preferably expressed by the respective codon-optimized polynucleotides as defined herein, such as preferably obtainable from *Pichia pastoris*.

As used herein, an increase in the percentage of 7-DHC within a sterol mix is defined as the amount of 7-DHC produced by a host cell expressing a heterologous polypeptide having desaturase activity as defined herein compared to a host cell with only expressing the endogenous C-5 sterol desaturase, such as e.g. expressed by ERG3. When using said host cell, e.g. yeast, in particular cholesterol-producing yeast cell, in a sterol production process, the percentage of 7-DHC can be increased to at least about 84% based on the total amount of sterols produced by said host cell. As used herein, "expression of an ERG3-homolog" includes the expression of extra-copies of ERG3 polypeptides, i.e. expression of two or more copies of ERG3, including extra-copies of endogenous ERG3.

In a particular embodiment, the invention is directed to a process for the production of a sterol mix wherein a yeast cells as described before is used and wherein the percentage of cholesta-8-enol and/or zymosterol and/or lanosterol and/or lathosterol present in said sterol mix is reduced, i.e. is in the range of about 16% or less based on the total amount of sterols, i.e. leading to higher ratio of 7-DHC in the sterol mix.

A modified host cell, which is capable of expressing the ERG3 homologs as defined herein, and further genes required for biosynthesis of vitamin D3 precursors and/or intermediates, is used in a process for production of vitamin D3 precursor 7-DHC. The modified host cell may be cultured in an aqueous medium supplemented with appropriate nutrients under aerobic or anaerobic conditions and as known by the skilled person for the respective cholesterol-producing host cells. Optionally, such cultivation is in the presence of proteins and/or co-factors involved in transfer of electrons, as known in the art. The cultivation/growth of the host cell may be conducted in batch, fed-batch, semi-continuous or continuous mode. Depending on the host cell, preferably, production of vitamin D3 and precursors thereof such as 7-DHC can vary, as it is known to the skilled person. Cultivation and isolation of 7-DHC and other intermediates in production of vitamin D3 is described in e.g. WO2011067144 or WO2017108799.

Using a host cell as described herein, the productivity/specificity of C-5 sterol desaturase activity could be shifted towards 7-DHC, leading to a ratio of at least about 84% 7-DHC in the total sterols produced by said host cell, with titers of up to about 10 g/l 7-DHC produced after about 110 h fermentation under suitable culture conditions.

The terms "ERG5" and "Erg5p" or "ERG6" and "Erg6p" are used interchangeably herein and refer to a polypeptide encoded by the respective genes erg3, erg5, and erg6.

Genes encoding ERG5, ERG6, ERG3, ARE1, ARE2, or sterol Δ24-reductase (ERG4), cultivation and genetic engineering of the yeast cell as used herein are known and described in e.g. U.S. Pat. No. 7,608,421.

As used herein, the terms "C-24-reductase" or "Δ24-reductase" are used interchangeably herein. In yeast, this enzyme is encoded by erg4 and is active on the methyl-group of the carbon atom on position 24. Trienol, which does not exhibit such methyl-group on said position, is therefore not an acceptable substrate for the yeast ERG4.

The terms "C-8 sterol isomerase", "enzyme having C-8 sterol isomerase activity" are used interchangeably herein and refer to enzymes which are capable of catalyzing the conversion of cholesta-8-enol into cholesta-7-enol and/or zymosterol into cholesta-7,24-dienol. In yeast, this enzyme is encoded by erg2. A preferred ERG2 homolog to be used in a modified host cell according to the present invention is a polypeptide having at least about 41%, such as e.g. at least 44, 45, 48, 49, 53, 56, 60, 70, 80, 90, 92, 95, 98 or up to 100% identity to SEQ ID NO:14 showing C-8 sterol isomerase activity and including a polynucleotide according to SEQ ID NO:14, showing C-8 sterol isomerase activity, including polynucleotides encoding such polypeptide, obtainable from *Ustilago maydis*. Particularly, 1 or more copies, such as at least 1, 2, 3, 5, of said ERG2 homolog are expressed in a modified host cell as defined herein.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in μmol substrate consumed or product formed per min per mg of protein. Typically, μmol/min is abbreviated by U (=unit). Therefore, the unit definitions for specific activity of μmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity, such as e.g. by HPLC.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code).

In particular, the present invention features the present embodiments:

1. A cholesterol-producing yeast cell comprising an enzyme having C5-sterol desaturase with at least about 45%, such as e.g. at least 50, 52, 60, 70, 80, 90, 92, 95, 98 or up to 100% identity to SEQ ID NO:2 being (heterologous) expressed in a suitable host cell for production of 7-DHC, wherein the ratio of 7-DHC to side-products including lanosterol and/or lathosterol is increased by at least about 5% compared to a non-modified host cell.
2. A cholesterol-producing yeast cell as above, comprising an enzyme having C5-sterol desaturase activity, said yeast cell producing a sterol mix comprising at least about 84% 7-dehydrocholesterol (7-DHC), preferably comprising at least about 85, 88, 90, 92, 95, 97, 98 or up to 100% 7-DHC based on the total amount of sterols.
3. A cholesterol-producing yeast cell as above, wherein the ratio of 7-DHC to cholesta-7-enol and/or lanosterol is in the range of about 18.
4. A cholesterol-producing yeast cell as above, wherein the ratio of 7-DHC to cholesta-7-enol and/or lanosterol is increased by at least about 5%.
5. A cholesterol-producing yeast cell as above expressing a heterologous enzyme having C5-sterol desaturase activity with at least about 45%, such as e.g. at least 50, 52, 60, 70, 80, 90, 92, 95, 98 or up to 100% identity to SEQ ID NO:2.
6. A cholesterol-producing yeast cell as above expressing a heterologous enzyme having C5-sterol desaturase activity, said enzyme being selected from the group consisting of *Saccharomyces*, such as *Saccharomyces cerevisiae*, *Yarrowia*, such as *Y. lipolytica*, Klyveromyces, such as *K. lactis*, *Schizosaccharomyces*, such as *Schizosaccharomyces pombe*, *Pichia*, such as *P. pastoris*, *Candida*, such as *C. albicans*, *Penicillium*, such as *P. roqueforti*, *Aspergillus*, such as *A. nidulans*, *Cryptococcus*, such as *C. neoformans*, Magneporte, Metarhizium and *Ustilago*, such as *Ustilago maydis*.
7. A cholesterol-producing yeast cell as above in which ERG5 and ERG6 are inactivated.
8. A cholesterol-producing yeast cell as above, wherein the yeast cell expresses a heterologous enzyme selected from EC 1.3.1.72 having sterol Δ24-reductase activity, preferably wherein the heterologous enzyme is originated from plant or vertebrate, more preferably originated from human, pig, dog, mouse, rat, horse or *Danio rerio*.
9. A cholesterol-producing yeast cell as above, wherein the yeast cell expresses a heterologous enzyme having C8-isomerase activity, preferably wherein the heterologous enzyme is obtainable from *Ustilago maydis*, more preferably from a polypeptide having at least about 42%, such as e.g. at least 43, 44, 47, 48, 49, 50, 51, 52, 53, 54, 55, 56, 75, 80, 90, 92, 95, 98 or up to 100% identity to the polypeptide according to SEQ ID NO:14.
10. Use of a cholesterol-producing yeast cell as above for production of sterols, preferably for the production of vitamin D3 precursors, more preferably for the production of 7-DHC.
11. Use of a cholesterol-producing yeast cell as above, wherein the 7-DHC is further converted into vitamin D3.
12. Use as above, wherein the 7-DHC is further converted into 25-hydroxyvitamin D3.
13. A process for reducing the amount of cholesta-7-enol and/or lanosterol in a sterol mix produced by a yeast cell, said process comprising expression of a heterologous enzyme having C5-sterol desaturase activity, said enzyme being selected from the group consisting of *Saccharomyces*, such as *Saccharomyces cerevisiae*, *Yarrowia*, such as *Y. lipolytica*, Klyveromyces, such as *K. lactis*, *Schizosaccharomyces*, such as *Schizosaccharomyces pombe*, *Pichia*, such as *P. pastoris*, *Candida*, such as *C. albicans*, *Penicillium*, such as *P. roqueforti*, *Aspergillus*, such as *A. nidulans*, *Cryptococcus*, such as *C. neoformans*, Magneporte, Metarhizium and *Ustilago*, such as *Ustilago maydis*, preferably selected from Pichia pastoris, Penicillium roqueforti, Schizosaccharomyces pombe, or Saccharomyces cerevisiae.

14. A process for the production of a sterol mix, preferably a vitamin D3-precursor, more preferably a sterol mix with at least about 84% 7-DHC, in a yeast cell comprising:

(a) inactivation of ERG5 and ERG6, (b) expressing of a heterologous enzyme selected from EC 1.3.1.72 having sterol Δ24-reductase activity on cholesta-7,24-dienol, zymosterol or trienol, preferably plant or vertebrate sterol Δ24-reductase, more preferably vertebrate sterol Δ24-reductase, (c) expression of a heterologous enzyme having C5-sterol desaturase activity, said enzyme being selected from the group consisting of *Saccharomyces*, such as *Saccharomyces cerevisiae*, *Yarrowia*, such as *Y. lipolytica*, *Klyveromyces*, such as *K. lactis*, *Schizosaccharomyces*, such as *Schizosaccharomyces pombe*, *Pichia*, such as *P. pastoris*, *Candida*, such as *C. albicans*, *Penicillium*, such as *P. roqueforti*, *Aspergillus*, such as *A. nidulans*, *Cryptococcus*, such as *C. neoformans*, Magneporte, Metarhizium and *Ustilago*, such as *Ustilago maydis*, preferably selected from *Pichia pastoris*, *Penicillium roqueforti*, *Schizosaccharomyces pombe*, or *Saccharomyces cerevisiae*, (d) cultivating said yeast cell under conditions suitable for sterol production; wherein the ratio of 7-DHC to cholesta-7-enol and/or lanosterol present in the sterol mix is more than 17.2.

The following examples are illustrative only and are not intended to limit the scope of the invention in any way.

EXAMPLES

Example 1: General Methods, Strains and Plasmids

All basic molecular biology and DNA manipulation procedures described herein were generally performed according to Sambrook et al. (1989. Molecular Cloning: A Laboratory Manual. Cold Spring Harbor Laboratory Press: New York) or Ausubel et al. (1998. Current Protocols in Molecular Biology. Wiley: New York). Genotypes of the used *S. cerevisiae* strains and plasmids are listed in Table 1 and 2. *Saccharomyces cerevisiae* 7-DHC producing strain Y2159 was constructed as described in Example 4. All listed strains are MATα.

TABLE 1

*Saccharomyces cerevisiae* strains.

| Y2159 | erg5Δ::PGK1p-S24R2-CYC1t-TRP1 erg6Δ::TDH3p-S24R1-PGK1t-URA3 erg4Δ::PGK1p-Scer-are1 G595D-CYC1t-LEU2 TDH3p-tHMG1 | See Example 4 |
|---|---|---|
| Y2346 | erg5Δ::PGK1p-S24R2-CYC1t-TRP1 erg6Δ::TDH3p-S24R1-PGK1t-URA3 erg4Δ::PGK1p-Scer-are1 G595D-CYC1t-LEU2 TDH3p-tHMG1 INT66 TDH3p-*S. cerevisiae*-ERG3-PGK1t-HYG$^R$ | Targeted insertion construct at INT66 locus |
| Y2322 | erg5Δ::PGK1p-S24R2-CYC1t-TRP1 erg6Δ::TDH3p-S24R1-PGK1t-URA3 erg4Δ::PGK1p-Scer-are1 G595D-CYC1t-LEU2 TDH3p-tHMG1 INT66 TDH3p-*P. pastoris*-ERG3-PGK1t-HYG$^R$ | Targeted insertion construct at INT66 locus |
| Y2316 | erg5Δ::PGK1p-S24R2-CYC1t-TRP1 erg6Δ::TDH3p-S24R1-PGK1t-URA3 erg4Δ::PGK1p-Scer-are1 G595D-CYC1t-LEU2 TDH3p-tHMG1 INT66 TDH3p-*P. roqueforti*-ERG3-PGK1t-HYG$^R$ | Targeted insertion construct at INT59 locus |
| Y2337 | erg5Δ::PGK1p-S24R2-CYC1t-TRP1 erg6Δ::TDH3p-S24R1-PGK1t-URA3 erg4Δ::PGK1p-Scer-are1 G595D-CYC1t-LEU2 TDH3p-tHMG1 INT66 TDH3p-*S. pombe*-ERG3-PGK1t-HYG$^R$ | Targeted insertion construct at INT66 locus |

TABLE 2 plasmids used for cloning of ERG3 homologs.

| Plasmid | Backbone | Insert | Oligos or source |
|---|---|---|---|
| pMB7722 | pMB7622 | *S. cerevisiae*-ERG3 | Synthesized fragment |
| pMB7700 | pMB7622 | *P. pastoris*-ERG3 | Synthesized fragment |
| pMB7721 | pMB7622 | *P. roqueforti*-ERG3 | Synthesized fragment |
| pMB7701 | pMB7622 | *S. pombe*-ERG3 | Synthesized fragment |

Example 2: Cloning of Various ERG3 Homologs into *S. cerevisiae* Y2159

All ERG3 cassettes were constructed as follows. Open reading frames were codon optimized based on the deduced amino acid sequence and synthesized with 5'-BamHI (GGATCCatg . . . ) sites and 3'-EcoRI sites). These were cloned by inserting BamHI-EcoRI-digested ERG3 fragments into BamHI-EcoRI-digested pMB7621, which allows targeting to the intergenic locus INT66 on the right arm of chromosome XIII between the RKR1 and GAD1 genes (ca. position 769,000).

Besides *S. cerevisiae* ERG3 (SEQ ID NO:7; plasmid pMB7677), the genes synthesized comprise ERG3 homologues (codon-optimized) from *Pichia pastoris* (SEQ ID NO:9; plasmid pMB7732), *Penicillium roqueforti* (SEQ ID NO:10; plasmid pMB7721), and *Schizosaccharomyces pombe* (SEQ ID NO:11; plasmid pMB7681), see sequence listing.

To test the impact of the different ERG3 genes in 7-DHC production, strain Y2159 was transformed with four different SfiI-generated fragments, representing one of the four species detailed above, at the INT66 locus using hygromycin resistance (HygR) as a selectable marker, and the strong constitutive TDH3-promoter as a controlling element.

Transformants were selected on YPD agar with 200 mg/L hygromycin after 3 days at 30° C. Strains resulting from these transformations are listed in Table 1 above. These strains were subsequently assayed for their 7-DHC productivity and overall 7-DHC sterol purity as described below.

Example 3: HPLC Analysis of Sterols from Transformed Strains

Strains were cultivated as follows. Strains to be tested were initially plated onto YPD agar and incubated for 48 hours at 30° C. Two milliliters YPD pre-cultures were inoculated from these plates and grown on a roller wheel for 24 hours at 30° C. In a 24-well microtiter plate, 0.8 mL of YPD+10 g/L ethanol were inoculated from the preculture to a final OD$_{600}$ of 0.5. Microtiter plates were grown at 30° C. in a humidified environment and shaking at 800 rpm on a shaker with an orbit of 3 mm. At 24 and 48 hours post-inoculation, 16 µl ethanol was added to each well as a feed. At 72 hours post-inoculation the cells were sampled for sterol content.

Sterols from the cultures were extracted and assayed as follows. Eighty microliters of whole broth was pipetted into a 2-mL Precellys tube with glass beads. Eight hundred microliters of saponification solution (5% KOH in ethanol) was added, and samples were placed into a Precellys 24 Homogenizer and agitated at 6500 rpm for 3 cycles at 15 seconds per cycle. Sixty microliters of glacial acetic acid were then added and the tubes were centrifuged for 1 minute at top speed. The supernatant was assayed via HPLC for sterol content. The results are shown in Table 3, 4, and 5.

TABLE 3 ratios of 7-DHC to zymosterol in control and strains carrying ERG3 homologs.

| Strain | Ratio 7-DHC to zymosterol |
| --- | --- |
| SC2159 - parent | 18.1 |
| P. pastoris ERG3 | 18.8 |

TABLE 3 ratios of 7-DHC to cholesta-8-enol in control and strains carrying ERG3 homologs.

| Strain | Ratio 7-DHC to cholesta-8-enol |
| --- | --- |
| SC2159 - parent | 11.7 |
| P. pastoris ERG3 | 12.1 |

TABLE 4 ratios of 7-DHC to mix of lanosterol and lathosterol in control and strains carrying ERG3 homologs.

| Strain | Ratio 7-DHC to lanosterol/lathosterol |
| --- | --- |
| SC2159 - parent | 17.2 |
| P. pastoris ERG3 | 22.9 |
| P. roqueforti ERG3 | 19.8 |
| S. pombe ERG3 | 18.1 |

Example 4: Construction of Y2159

WT *S. cerevisiae* ARE1 was synthesized by DNA2.0, incorporating an XbaI site at the 5' end (TCTAGAACAAAatg . . . ) and a PstI site at the 3'end. This was cloned into an erg4Δ::HygR deletion plasmid using unique XbaI and PstI sites. LEU2 was subsequently used to replace the HygR moiety via a KpnI-AgeI cloning. The result was plasmid pHyD459.

*S. cerevisiae* ARE1 mutant variant pMB7584 (F592L) was generated by ligating a BsrGI-BsaI-cleaved PCR product generated from ARE1 (oligos according to SEQ ID NO:16 & 17) with a double-stranded oligo derived by annealing SEQ ID NO:19 and 20 into BsrGI-PstI-cleaved pHyD459. Similarly, *S. cerevisiae* ARE1 mutant variant pMB7585 (G595D) was generated by ligating a BsrGI-BsaI-cleaved PCR product generated from ARE1 (oligos according to SEQ ID NO:16 & 18) with a double-stranded oligo derived by annealing SEQ ID NO:21 and 22 into BsrGI-PstI-cleaved pHyD459. The oligos as well as further sequences used herein are listed in Table 5.

TABLE 5 plasmids used for construction of ARE mutations. "Scer" means Saccharomyces cerevisiae.

| Plasmid | Backbone | Insert | Oligos or source | SEQ ID NO |
| --- | --- | --- | --- | --- |
| pHyD459 | pHyD445 | Scer-ARE1 | LEU2 insertion | |
| pMB7584 | pHyD459 | Scer-are1 F592L | MO10013 & MO10014, MO10016 & MO10017 | 16 & 17 19 & 20 |
| pMB7585 | pHyD459 | Scer-are1 G595D | MO10013 & MO10015 | 16 & 18 |

The invention claimed is:

1. A cholesterol-producing yeast cell expressing (i) a heterologous C5-sterol desaturase with at least 90% sequence identity to SEQ ID NO: 2, 4, 6 or 8 and (ii) a heterologous C8-isomerase with at least 90% sequence identity to SEQ ID NO:_14, wherein the yeast cell is capable of producing a sterol mix comprising 7-dehydrocholesterol (7-DHC), lanosterol, and lathosterol, wherein the ratio of 7-DHC to lanosterol and lathosterol combined is at least 5% higher than the ratio of 7-DHC to lanosterol and lathosterol combined in a sterol mix produced by a reference yeast cell that does not express the heterologous C5-sterol desaturase and C8-isomerase.

2. The cholesterol-producing yeast cell according to claim 1, wherein at least 84% of the sterol mix produced is 7-DHC.

3. The cholesterol-producing yeast cell according to claim 1, wherein 7-DHC is produced at a ratio to lanosterol of 18 or more.

4. The cholesterol-producing yeast cell according to claim 1, wherein the heterologous C5-sterol desaturase is from *S. cerevisiae, Y. lipolytica, K. lactis, S. pombe, P. pastoris, C. albicans, P. roqueforti, A. nidulans, C. neoformans, M. oryzae, M. acridum*, or *U. maydis*.

5. The cholesterol-producing yeast cell according to claim 1 in which ERG5 and ERG6 are inactivated.

6. The cholesterol-producing yeast cell according to claim 1, wherein the yeast cell further expresses a heterologous plant or vertebrate sterol 424-reductase.

7. A process for production of 7-DHC, comprising cultivating the yeast cell according to claim 1 under conditions suitable for sterol production.

8. The process according to claim 7, wherein the 7-DHC is further converted into vitamin D3.

9. The process according to claim 7, wherein the 7-DHC is further converted into 25-hydroxyvitamin D3.

10. A process for production of a sterol mix, said process comprising cultivating the yeast cell according to claim 4 under conditions suitable for sterol production.

11. A process for production of a sterol mix, comprising cultivating the yeast cell according to claim 6 under conditions suitable for sterol production, wherein
   (a) ERG5 and ERG6 are inactivated in the yeast cell,
   (b) the heterologous sterol Δ24-reductase is a vertebrate sterol Δ24-reductase, and
   (c) the heterologous C5-sterol desaturase is from *Pichia pastoris, Penicillium roqueforti, Schizosaccharomyces pombe*, or *Saccharomyces cerevisiae*.

12. The cholesterol-producing yeast cell according to claim 1,
   wherein
   (a) the heterologous C5-sterol desaturase is from *Pichia pastoris, Penicillium roqueforti, Schizosaccharomyces pombe*, or *Saccharomyces cerevisiae*,
   (b) ERG5 and ERG6 are inactivated in the yeast cell, and
   (c) the yeast cell expresses a heterologous vertebrate sterol Δ24-reductase.

13. A process for production of a sterol mix comprising cultivating the yeast cell according to claim 12 under conditions suitable for sterol production.

* * * * *

UNITED STATES PATENT AND TRADEMARK OFFICE
CERTIFICATE OF CORRECTION

| | |
|---|---|
| PATENT NO. | : 12,018,309 B2 |
| APPLICATION NO. | : 17/051610 |
| DATED | : June 25, 2024 |
| INVENTOR(S) | : Christopher Mark Farrell et al. |

It is certified that error appears in the above-identified patent and that said Letters Patent is hereby corrected as shown below:

In the Claims

Column 39, Line 16, Claim 1: Please change "SEQ ID NO:_14" to --SEQ ID NO: 14--

Signed and Sealed this
Fifteenth Day of October, 2024

Katherine Kelly Vidal
*Director of the United States Patent and Trademark Office*

SEQUENCE LISTING

<160> NUMBER OF SEQ ID NOS: 22

<210> SEQ ID NO 1
<211> LENGTH: 1155
<212> TYPE: DNA
<213> ORGANISM: Pichia pastoris

<400> SEQUENCE: 1

```
atggacattg ctttggagat tctagacact tttgtctttg acaaagtcta tgcaaaacta      60
ctgcccattt ctctggtgca acatttgcca gatggctatt tgaagacttt gggacatttg     120
actggtgcca acaacaccat ggaatcactg ttcggaatag ctccaaacgt tgaccaagcg     180
tctaagaacc actggctgag aacagtgaat gactctattg ccttagcccg tcccggtgag     240
cgtctggtct acggtgtcaa cgctccttta cacttttttg acgaaacagc gtatacatac     300
gcatcgatct tgggacgctc caatatcatt cgacaattca caactttgat gattctgatg     360 attcttttg gctggggttt gtatttatct gtggcttcat tttcatacta ctttgttttt     420
gataaagcca ttttcaatca cccaagatac ctcaaaaaacc agatgtctct ggagatccat     480
```

-continued

| | |
|---|---|
| caagcgttga ctgctatacc tacgatggtt ttgcttacag ttccatggtt tttgattgag | 540 |
| ttgcgtggat actctaaatt atactttgat gtaaatgagt ctactggagg atggaaggct | 600 |
| attatttggc aaattccttg cttcattatg tttaccgatt gttgtatcta ctttattcat | 660 |
| cgttggttgc actggccatc cgtgtataag cgtttgcaca agcctcacca caagtggatt | 720 |
| gtttgtacac cttttgctag tcatgccttc catccagttg atggttatgc acaatcacta | 780 |
| ccttaccatt tgtatggaat gttgtttcca ctacacaagg tgagctatct gatcttatt | 840 |
| gggcttgtga acttttggac tgttatgatc catgatggag aatacctgtc cagagaccct | 900 |
| atagtcaatg gagctgcttg tcatacagtg catcacctat acttcaacta caattacggc | 960 |
| cagttcacaa cactttggga ccgtcttggt ggatcataca gaatgccaga caaggaactc | 1020 |
| tttgataaga acaagaagaa agatgtaaag acatggcgtt cacaagtcaa gcaggccgat | 1080 |
| tcgataagag aagacttaga gggaaaagaa gatttccgtg agtatggaac tgaggaaaaa | 1140 |
| cttaaaagca catag | 1155 |

<210> SEQ ID NO 2
<211> LENGTH: 384
<212> TYPE: PRT
<213> ORGANISM: Pichia pastoris

<400> SEQUENCE: 2

Met Asp Ile Ala Leu Glu Ile Leu Asp Thr Phe Val Phe Asp Lys Val
1               5                   10                  15

Tyr Ala Lys Leu Leu Pro Ile Ser Leu Val Gln His Leu Pro Asp Gly
            20                  25                  30

Tyr Leu Lys Thr Leu Gly His Leu Thr Gly Ala Asn Asn Thr Met Glu
        35                  40                  45

Ser Leu Phe Gly Ile Ala Pro Asn Val Asp Gln Ala Ser Lys Asn His
    50                  55                  60

Trp Leu Arg Thr Val Asn Asp Ser Ile Ala Leu Ala Arg Pro Gly Glu
65                  70                  75                  80

Arg Leu Val Tyr Gly Val Asn Ala Pro Leu His Phe Phe Asp Glu Thr
                85                  90                  95

Ala Tyr Thr Tyr Ala Ser Ile Leu Gly Arg Ser Asn Ile Ile Arg Gln
            100                 105                 110

Phe Thr Thr Leu Met Ile Leu Met Ile Leu Phe Gly Trp Gly Leu Tyr
        115                 120                 125

Leu Ser Val Ala Ser Phe Ser Tyr Tyr Phe Val Phe Asp Lys Ala Ile
    130                 135                 140

Phe Asn His Pro Arg Tyr Leu Lys Asn Gln Met Ser Leu Glu Ile His
145                 150                 155                 160

Gln Ala Leu Thr Ala Ile Pro Thr Met Val Leu Leu Thr Val Pro Trp
                165                 170                 175

Phe Leu Ile Glu Leu Arg Gly Tyr Ser Lys Leu Tyr Phe Asp Val Asn
            180                 185                 190

Glu Ser Thr Gly Gly Trp Lys Ala Ile Ile Trp Gln Ile Pro Cys Phe
        195                 200                 205

Ile Met Phe Thr Asp Cys Cys Ile Tyr Phe Ile His Arg Trp Leu His
    210                 215                 220

Trp Pro Ser Val Tyr Lys Arg Leu His Lys Pro His Lys Trp Ile
225                 230                 235                 240

Val Cys Thr Pro Phe Ala Ser His Ala Phe His Pro Val Asp Gly Tyr
                245                 250                 255

```
Ala Gln Ser Leu Pro Tyr His Leu Tyr Gly Met Leu Phe Pro Leu His
            260                 265                 270

Lys Val Ser Tyr Leu Ile Leu Phe Gly Leu Val Asn Phe Trp Thr Val
        275                 280                 285

Met Ile His Asp Gly Glu Tyr Leu Ser Arg Asp Pro Ile Val Asn Gly
    290                 295                 300

Ala Ala Cys His Thr Val His His Leu Tyr Phe Asn Tyr Asn Tyr Gly
305                 310                 315                 320

Gln Phe Thr Thr Leu Trp Asp Arg Leu Gly Gly Ser Tyr Arg Met Pro
                325                 330                 335

Asp Lys Glu Leu Phe Asp Lys Asn Lys Lys Asp Val Lys Thr Trp
            340                 345                 350

Arg Ser Gln Val Lys Gln Ala Asp Ser Ile Arg Glu Asp Leu Glu Gly
        355                 360                 365

Lys Glu Asp Phe Arg Glu Tyr Gly Thr Glu Glu Lys Leu Lys Ser Thr
370                 375                 380
```

<210> SEQ ID NO 3
<211> LENGTH: 939
<212> TYPE: DNA
<213> ORGANISM: Penicillium roqueforti

<400> SEQUENCE: 3

```
atggatattt tcctggacgt tctagatact ttggtcctcg accggtgcta cgcagtactc      60
tcgccagacc caacagccat ctccaacaat gatactcaag ccactgccca tttgaaccaa     120
catgtcgggg tatattaccc tatgcagccc tcgaagtggg cggaggcaag cctctggaag     180
agagacgaca ttgccagaca agcattgtca ctgtacgtga ttatatggct tttcgcaatg     240
ataatgtacc tcctcggtag ccttctccta tatcacaccc tcttcgacaa aagactactc     300
caacacccgc gcttcctcgc acaccaagtc aagctcgaga tcaaccaagg catctccgca     360
atcccagtca tggccctcct caccgtccca ttctttctag ctgagataag gggctggtcg     420
aagctatatg atctcaccag cgactccccg ttcttcggat acaccttgct ccagtatcca     480
ttgttcatct gcttcacaga tagtggcatt tactggatac accgtggtct gcatcatcct     540
agcgtctatc gctggcttca caagccacac cataaatggg cggtgccgac tccgttcgct     600
agttatgcgt tcaccctct ggatggatgg gcgcagagtc tcccctacca tgtttacccg     660
ttgctctttc cgttgcagaa gggagcatat ctgggactgt ttatgtttgt cactgtgtgg     720
acggtgctga ttcacgacgc tgagtacttg ccaacatcgg tggtaatcaa cggcgcttct     780
tgtcacacga tgcatcactt gtacttcaat tacaattacg ggcagtttac aacggcatgg     840
gatcgcctcg cgggaacata ccgaaagcct aaggggata gtttcatgga aggtcagcaa     900
atggatggga aagggaaact cggaggtaag tgtgaatag                             939
```

<210> SEQ ID NO 4
<211> LENGTH: 312
<212> TYPE: PRT
<213> ORGANISM: Penicillium roqueforti

<400> SEQUENCE: 4

```
Met Asp Ile Phe Leu Asp Val Leu Asp Thr Leu Val Leu Asp Arg Cys
1               5                   10                  15

Tyr Ala Val Leu Ser Pro Asp Pro Thr Ala Ile Ser Asn Asn Asp Thr
            20                  25                  30
```

```
Gln Ala Thr Ala His Leu Asn Gln His Val Gly Val Tyr Tyr Pro Met
             35                  40                  45

Gln Pro Ser Lys Trp Ala Glu Ala Ser Leu Trp Lys Arg Asp Asp Ile
 50                  55                  60

Ala Arg Gln Ala Leu Ser Leu Tyr Val Ile Ile Trp Leu Phe Ala Met
 65                  70                  75                  80

Ile Met Tyr Leu Leu Gly Ser Leu Leu Leu Tyr His Thr Leu Phe Asp
                 85                  90                  95

Lys Arg Leu Leu Gln His Pro Arg Phe Leu Ala His Gln Val Lys Leu
            100                 105                 110

Glu Ile Asn Gln Gly Ile Ser Ala Ile Pro Val Met Ala Leu Leu Thr
            115                 120                 125

Val Pro Phe Phe Leu Ala Glu Ile Arg Gly Trp Ser Lys Leu Tyr Asp
130                 135                 140

Leu Thr Ser Asp Ser Pro Phe Phe Gly Tyr Thr Leu Leu Gln Tyr Pro
145                 150                 155                 160

Leu Phe Ile Cys Phe Thr Asp Ser Gly Ile Tyr Trp Ile His Arg Gly
                165                 170                 175

Leu His His Pro Ser Val Tyr Arg Trp Leu His Lys Pro His His Lys
            180                 185                 190

Trp Ala Val Pro Thr Pro Phe Ala Ser Tyr Ala Phe His Pro Leu Asp
            195                 200                 205

Gly Trp Ala Gln Ser Leu Pro Tyr His Val Tyr Pro Leu Leu Phe Pro
210                 215                 220

Leu Gln Lys Gly Ala Tyr Leu Gly Leu Phe Met Phe Val Thr Val Trp
225                 230                 235                 240

Thr Val Leu Ile His Asp Ala Glu Tyr Leu Pro Thr Ser Val Val Ile
                245                 250                 255

Asn Gly Ala Ser Cys His Thr Met His His Leu Tyr Phe Asn Tyr Asn
            260                 265                 270

Tyr Gly Gln Phe Thr Thr Ala Trp Asp Arg Leu Ala Gly Thr Tyr Arg
            275                 280                 285

Lys Pro Lys Gly Asp Ser Phe Met Glu Gly Gln Gln Met Asp Gly Lys
290                 295                 300

Gly Lys Leu Gly Gly Lys Cys Glu
305                 310

<210> SEQ ID NO 5
<211> LENGTH: 903
<212> TYPE: DNA
<213> ORGANISM: Schizosaccharomyces pombe

<400> SEQUENCE: 5
atggactacc tactcaacta tgctgaccaa tatgcgctgg attcgatata caatgctgta    60
tatccattag ctcgcgacaa tatcgttaga cagtcgatca gtttgttttt tttaacttgg   120
tttggcggta tgttcttgta tttaacattt gcgtcgcttt cctaccaatt tgtgtttgat   180
aaaagtctga tggatcaccc aaagttctta aaaaaccagg tgttcatgga agttctaacg   240
gctttacaaa acttacctgg tatggcgtta ttgacggttc cgtggttttt ggctgagttg   300
catgggtaca gctacttata cgacaacatc agtgattacg gtttaaaata cttcttatgt   360
tccttacctc tttttgtcat gttctcagat tttggcattt actgggctca tcgtttcctt   420
catcaccgtt atgtataccc tcgtcttcac aaactccatc ataagtggat tatctgcact   480
ccatatgcat cccatgcttt caaatccgct gatggcttct acaatctctc tccttaccat   540
```

```
cttttcccct ttttctttcc ccttcacaag ttgacctact tggctctttt cacctttgtc    600
aacttctggt ccatcatgat tcacgatggt aaatacatct ccaacaaccc catcatcaat    660
ggtgctgctc accataatgg ccatcacatt tatttcaact acaattacgg ccaattcacc    720
accctctttg atcgcctcgg caactctttc cgggcccccg atgaggcatg gtttgacaaa    780
gatcttcgcc aaaacgagga tgttcttcgt gtcgaattga tggagtacga ggctattcgt    840
aatgaagttg aagtgatga tgatagagaa tacatcgcta actctgctaa gaagaaccat    900
taa                                                                 903
```

<210> SEQ ID NO 6
<211> LENGTH: 300
<212> TYPE: PRT
<213> ORGANISM: Schizosaccharomyces pombe

<400> SEQUENCE: 6

```
Met Asp Tyr Leu Leu Asn Tyr Ala Asp Gln Tyr Ala Leu Asp Ser Ile
1               5                   10                  15

Tyr Asn Ala Val Tyr Pro Leu Ala Arg Asp Asn Ile Val Arg Gln Ser
            20                  25                  30

Ile Ser Leu Phe Phe Leu Thr Trp Phe Gly Met Phe Leu Tyr Leu
        35                  40                  45

Thr Phe Ala Ser Leu Ser Tyr Gln Phe Val Phe Asp Lys Ser Leu Met
    50                  55                  60

Asp His Pro Lys Phe Leu Lys Asn Gln Val Phe Met Glu Val Leu Thr
65                  70                  75                  80

Ala Leu Gln Asn Leu Pro Gly Met Ala Leu Leu Thr Val Pro Trp Phe
                85                  90                  95

Leu Ala Glu Leu His Gly Tyr Ser Tyr Leu Tyr Asp Asn Ile Ser Asp
            100                 105                 110

Tyr Gly Leu Lys Tyr Phe Leu Cys Ser Leu Pro Leu Phe Val Met Phe
        115                 120                 125

Ser Asp Phe Gly Ile Tyr Trp Ala His Arg Phe Leu His His Arg Tyr
130                 135                 140

Val Tyr Pro Arg Leu His Lys Leu His Lys Trp Ile Ile Cys Thr
145                 150                 155                 160

Pro Tyr Ala Ser His Ala Phe Lys Ser Ala Asp Gly Phe Leu Gln Ser
                165                 170                 175

Leu Pro Tyr His Leu Phe Pro Phe Phe Pro Leu His Lys Leu Thr
            180                 185                 190

Tyr Leu Ala Leu Phe Thr Phe Val Asn Phe Trp Ser Ile Met Ile His
        195                 200                 205

Asp Gly Lys Tyr Ile Ser Asn Asn Pro Ile Ile Asn Gly Ala Ala His
    210                 215                 220

His Asn Gly His His Ile Tyr Phe Asn Tyr Asn Tyr Gly Gln Phe Thr
225                 230                 235                 240

Thr Leu Phe Asp Arg Leu Gly Asn Ser Phe Arg Ala Pro Asp Glu Ala
                245                 250                 255

Trp Phe Asp Lys Asp Leu Arg Gln Asn Glu Asp Val Leu Arg Val Glu
            260                 265                 270

Leu Met Glu Tyr Glu Ala Ile Arg Asn Glu Val Glu Gly Asp Asp
        275                 280                 285

Arg Glu Tyr Ile Ala Asn Ser Ala Lys Lys Asn His
    290                 295                 300
```

<210> SEQ ID NO 7
<211> LENGTH: 1098
<212> TYPE: DNA
<213> ORGANISM: Saccharomyces cerevisiae

<400> SEQUENCE: 7

```
atggatttgg tcttagaagt cgctgaccat tatgtcttag acgacttgta cgctaaagtt      60
ctgcccgctt cgttggcagc taatattcct gtcaagtggc agaaattgct agggttgaac     120
agtgggttca gcaattctac gattttgcag gagactttga actccaagaa tgccgtcaaa     180
gaatgtagaa ggttctacgg gcaggtgcca ttcctgtttg atatgtcgac gacgtctttt     240
gcatcgctat tgcctcgttc cagcatcttg agagaattcc tctcactatg ggttattgtt     300
acgatctttg gttactact ttacttattc acggctagtc tcagctacgt gtttgtgttt     360
gacaagtcga ttttcaacca tcctcgttac ttgaaaaacc aaatggcaat ggaaatcaag     420
ttggcagtca gtgctatccc atggatgtcg atgttgaccg ttccatggtt tgttatggaa     480
ttgaacggcc attctaaact atacatgaag attgattatg aaaaccacgg tgtaaggaag     540
ctcattatcg agtacttcac tttcatcttt ttcactgatt gcggtgtgta tttagcgcac     600
agatggttgc attggccaag ggtctaccgt gctctgcaca agcctcatca aagtggctg     660
gtctgcacac ctttcgcatc tcattctttc catcctgtag acgggttttt gcaatccatc     720
tcgtaccaca tctacccatt gattctgcca ttacacaagg tttcttattt gattctgttc     780
acttttgtta acttttggac tgttatgatt catgacggtc aataccatc aaacaatcct     840
gccgtcaacg gtactgcctg ccacacggtt caccatctat atttcaacta caactacggt     900
caattcacca ctctgtggga cagactaggg ggttcttacc gtagaccaga tgactcattg     960
tttgatccta agttaagaga tgctaaggag acctgggacg ctcaagttaa ggaagttgaa    1020
catttcatca aggaggtcga aggtgatgat aatgatagaa tctatgaaaa cgacccaaat    1080
accaagaaga acaactga                                                 1098
```

<210> SEQ ID NO 8
<211> LENGTH: 365
<212> TYPE: PRT
<213> ORGANISM: Saccharomyces cerevisiae

<400> SEQUENCE: 8

```
Met Asp Leu Val Leu Glu Val Ala Asp His Tyr Val Leu Asp Asp Leu
1               5                   10                  15

Tyr Ala Lys Val Leu Pro Ala Ser Leu Ala Ala Asn Ile Pro Val Lys
            20                  25                  30

Trp Gln Lys Leu Leu Gly Leu Asn Ser Gly Phe Ser Asn Ser Thr Ile
        35                  40                  45

Leu Gln Glu Thr Leu Asn Ser Lys Asn Ala Val Lys Glu Cys Arg Arg
    50                  55                  60

Phe Tyr Gly Gln Val Pro Phe Leu Phe Asp Met Ser Thr Thr Ser Phe
65                  70                  75                  80

Ala Ser Leu Leu Pro Arg Ser Ser Ile Leu Arg Glu Phe Leu Ser Leu
                85                  90                  95

Trp Val Ile Val Thr Ile Phe Gly Leu Leu Tyr Leu Phe Thr Ala
            100                 105                 110

Ser Leu Ser Tyr Val Phe Val Phe Asp Lys Ser Ile Phe Asn His Pro
        115                 120                 125
```

```
Arg Tyr Leu Lys Asn Gln Met Ala Met Glu Ile Lys Leu Ala Val Ser
            130                 135                 140

Ala Ile Pro Trp Met Ser Met Leu Thr Val Pro Trp Phe Val Met Glu
145                 150                 155                 160

Leu Asn Gly His Ser Lys Leu Tyr Met Lys Ile Asp Tyr Glu Asn His
                165                 170                 175

Gly Val Arg Lys Leu Ile Ile Glu Tyr Phe Thr Phe Ile Phe Phe Thr
            180                 185                 190

Asp Cys Gly Val Tyr Leu Ala His Arg Trp Leu His Trp Pro Arg Val
        195                 200                 205

Tyr Arg Ala Leu His Lys Pro His His Lys Trp Leu Val Cys Thr Pro
210                 215                 220

Phe Ala Ser His Ser Phe His Pro Val Asp Gly Phe Leu Gln Ser Ile
225                 230                 235                 240

Ser Tyr His Ile Tyr Pro Leu Ile Leu Pro Leu His Lys Val Ser Tyr
                245                 250                 255

Leu Ile Leu Phe Thr Phe Val Asn Phe Trp Thr Val Met Ile His Asp
            260                 265                 270

Gly Gln Tyr Leu Ser Asn Asn Pro Ala Val Asn Gly Thr Ala Cys His
        275                 280                 285

Thr Val His His Leu Tyr Phe Asn Tyr Asn Tyr Gly Gln Phe Thr Thr
290                 295                 300

Leu Trp Asp Arg Leu Gly Gly Ser Tyr Arg Arg Pro Asp Asp Ser Leu
305                 310                 315                 320

Phe Asp Pro Lys Leu Arg Asp Ala Lys Glu Thr Trp Asp Ala Gln Val
                325                 330                 335

Lys Glu Val Glu His Phe Ile Lys Glu Val Glu Gly Asp Asp Asn Asp
            340                 345                 350

Arg Ile Tyr Glu Asn Asp Pro Asn Thr Lys Lys Asn Asn
        355                 360                 365

<210> SEQ ID NO 9
<211> LENGTH: 1155
<212> TYPE: DNA
<213> ORGANISM: Artificial Sequence
<220> FEATURE:
<223> OTHER INFORMATION: S. cerevisiae codon-optimized Pichia pastoris
      ERG3

<400> SEQUENCE: 9
atggatatcg ctttggaaat cttggatacc tttgttttcg acaaggttta tgctaaattg      60
ttgccaattt ccttggtcca acatttgcca gatggttact tgaaaacctt gggtcatttg     120
actggtgcca acaacaccat ggaatccttg ttcggtattg ctccaaacgt tgaccaagcc     180
tctaagaacc actggttgcg tactgttaac gattccattg ctttggccag acctggtgaa     240
cgtttggtct acggtgtcaa cgctcctttg cattttttcg atgaaaccgc ttatacttac     300
gcttccatct tgggtcgttc caatatcatt cgtcaattca ctactttgat gatcttgatg     360
attttgttcg gttggggttt gtatttgtct gtcgcttctt tttcctatta ctttgttttt     420
gataaggcta ttttcaacca tccaagatac ttgaagaacc aaatgtcctt ggaaatccat     480
caagccttga ctgctattcc taccatggtt tgttgactg ttccatggtt tttgatcgaa     540
ttgcgtggtt actctaagtt atactttgat gttaatgaat ccactggtgg ttggaaggct     600
attatttggc aaaattcctt gtttcattat gtttaccgatt gttgtatcta ctttattcat     660
cgttggttgc actggccatc cgtttacaag cgtttgcaca agcctcacca caagtggatt     720
```

```
gtttgtactc catttgcttc tcatgccttc catccagttg atggttatgc tcaatctttg    780
ccttaccatt tgtatggtat gttgtttcca ttgcacaagg tttcctactt gatcttgttt    840
ggtttggtca acttttggac tgttatgatc catgatggtg aatacttgtc ccgtgatcct    900
attgtcaatg gtgctgcttg tcatactgtc catcacttgt acttcaacta caattacggt    960
caattcacta ctttgtggga ccgtttgggt ggttcttaca gaatgccaga caaggaattg   1020
ttcgataaga acaagaagaa agatgttaag acttggcgtt ctcaagtcaa gcaagccgac   1080
tctattagag aagacttgga aggtaaagaa gatttccgtg aatacggtac tgaagaaaaa   1140
ttgaaatcca cctaa                                                    1155
```

<210> SEQ ID NO 10
<211> LENGTH: 939
<212> TYPE: DNA
<213> ORGANISM: Artificial Sequence
<220> FEATURE:
<223> OTHER INFORMATION: S. cerevisiae codon-optimized Pencicillium
      roqueforti ERG3

<400> SEQUENCE: 10

```
atggatattt tcttggacgt tttggatact ttggtcttgg acagatgcta cgctgtcttg     60
tccccagacc caactgccat ctccaacaat gatactcaag ccactgccca tttgaaccaa    120
catgtcggtg tctattaccc tatgcaacct tccaagtggg ccgaagcctc cttgtggaag    180
cgtgatgaca ttgccagaca agccttgtcc ttgtacgtca ttatttggtt gttcgctatg    240
attatgtact tgtttgggttc cttgttgttg taccatacct tgttcgacaa agattgttg    300 caacacccaa gattcttggc ccaccaagtc aagttggaaa tcaaccaagg tatctccgct    360
atcccagtca tggccttgtt gaccgtccca ttcttttttgg ctgaaatccg tggttggtcc    420
aagttgtatg acttgaccctc cgactccccca ttcttcggtt acaccttgtt gcaataccca    480
ttgttcatct gcttcactga ttccggtatt tactggattc accgtggttt gcaccatcct    540
tccgtctacc gttggttgca aagccacac cataaatggg ccgtccctac cccttttcgct   600 tcttatgctt ccaccccttt ggacggttgg gcccaatcct tgccatacca tgtttaccca    660 tgttgttcc cattgcaaaa gggtgcttac ttgggtttgt tcatgtttgt cactgtctgg    720
accgtcttga tccatgacgc cgaatacttg ccaacctctg tcgttatcaa cggtgcctct    780
tgtcacacca tgcatcactt gtacttcaat tacaattacg gtcaattcac tactgcctgg    840
gaccgtttgg ccggtactta ccgtaagcct aagggtgact ctttcatgga aggtcaacaa    900
atggacggta aggtaagtt gggtggtaag tgtgaataa                           939
```

<210> SEQ ID NO 11
<211> LENGTH: 990
<212> TYPE: DNA
<213> ORGANISM: Artificial Sequence
<220> FEATURE:
<223> OTHER INFORMATION: S. cerevisiae codon-optimized
      Schizosaccharomyces pombe ERG3

<400> SEQUENCE: 11

```
atggatgttg tcttgcaata cgctgataaa tacgttttg acaccttta cggtaagatt     60 gctgaatcct tcgattcctc ttcctctttt gctaatactg ctgttaattc taccaccttg    120
ggtttggctg aaaaggttaa ctttgctatc acctccggtt tgttagatcg taacaatgtc    180
tggcgtcaat tcacctcctt gttcttgatc acctggatta tgggtacttt gtcttacttt    240
```

-continued

```
ttgtctgcct cttttgctta ttacgtttac tttgatcgtg aagaagccag acgtcaccct    300
aagttttga aaaccaaga acacttggaa ttgatggttg ctttgaaaaa cttgccaggt    360
atggctattt tgaccgctcc ttggttctta gctgaaattc gtggttatgg ttatgtttat    420
gataagttgg atgaatatgg ttatttctat ttgttctttt ccatcgcctt gttcttgttg    480
ttttctgatt ttttgattta ctggattcac cgtgctttgc atcatcgttg ttgtacgct    540
cctttgcata agttgcatca caaatggatt gttccaactc cttactcttc tcacgctttt    600
cattatttgg atggttactc tcaatccttg ccatatcata tgttcccatt tttcttccca    660
ttaaacaaat acgtttattt gttgttgttt ggttctgtta attactggac tgtcttgatc    720
cacgacggta agtactttc taacaacgct gtcgttaatg gtgctgctca tcacgctgct    780
caccatatgt actttaacta taactatggt caattcttca ccttgtttga tcgtttgtgc    840
tcttcttaca gacaaccaga ccaagaatta ttcgatgccg aattgcgtaa cgaaaaattg    900
caagaacaac gtatccgttt catggaaact gtccaatata ccgtcgaagg taaagatgac    960
cgtacttacg cttccaagaa ggataactaa                                     990
```

<210> SEQ ID NO 12
<211> LENGTH: 610
<212> TYPE: PRT
<213> ORGANISM: Saccharomyces cerevisiae

<400> SEQUENCE: 12

```
Met Thr Glu Thr Lys Asp Leu Leu Gln Asp Glu Glu Phe Leu Lys Ile
1               5                   10                  15

Arg Arg Leu Asn Ser Ala Glu Ala Asn Lys Arg His Ser Val Thr Tyr
            20                  25                  30

Asp Asn Val Ile Leu Pro Gln Glu Ser Met Glu Val Ser Pro Arg Ser
        35                  40                  45

Ser Thr Thr Ser Leu Val Glu Pro Val Glu Ser Thr Glu Gly Val Glu
    50                  55                  60

Ser Thr Glu Ala Glu Arg Val Ala Gly Lys Gln Glu Gln Glu Glu Glu
65                  70                  75                  80

Tyr Pro Val Asp Ala His Met Gln Lys Tyr Leu Ser His Leu Lys Ser
                85                  90                  95

Lys Ser Arg Ser Arg Phe His Arg Lys Asp Ala Ser Lys Tyr Val Ser
            100                 105                 110

Phe Phe Gly Asp Val Ser Phe Asp Pro Arg Pro Thr Leu Leu Asp Ser
        115                 120                 125

Ala Ile Asn Val Pro Phe Gln Thr Thr Phe Lys Gly Pro Val Leu Glu
    130                 135                 140

Lys Gln Leu Lys Asn Leu Gln Leu Thr Lys Thr Lys Thr Lys Ala Thr
145                 150                 155                 160

Val Lys Thr Thr Val Lys Thr Thr Glu Lys Thr Asp Lys Ala Asp Ala
                165                 170                 175

Pro Pro Gly Glu Lys Leu Glu Ser Asn Phe Ser Gly Ile Tyr Val Phe
            180                 185                 190

Ala Trp Met Phe Leu Gly Trp Ile Ala Ile Arg Cys Cys Thr Asp Tyr
        195                 200                 205

Tyr Ala Ser Tyr Gly Ser Ala Trp Asn Lys Leu Glu Ile Val Gln Tyr
    210                 215                 220

Met Thr Thr Asp Leu Phe Thr Ile Ala Met Leu Asp Leu Ala Met Phe
225                 230                 235                 240
```

Leu Cys Thr Phe Phe Val Val Phe Val His Trp Leu Val Lys Lys Arg
                245                 250                 255

Ile Ile Asn Trp Lys Trp Thr Gly Phe Val Ala Val Ser Ile Phe Glu
        260                 265                 270

Leu Ala Phe Ile Pro Val Thr Phe Pro Ile Tyr Val Tyr Tyr Phe Asp
            275                 280                 285

Phe Asn Trp Val Thr Arg Ile Phe Leu Phe Leu His Ser Val Val Phe
    290                 295                 300

Val Met Lys Ser His Ser Phe Ala Phe Tyr Asn Gly Tyr Leu Trp Asp
305                 310                 315                 320

Ile Lys Gln Glu Leu Glu Tyr Ser Ser Lys Gln Leu Gln Lys Tyr Lys
                325                 330                 335

Glu Ser Leu Ser Pro Glu Thr Arg Glu Ile Leu Gln Lys Ser Cys Asp
            340                 345                 350

Phe Cys Leu Phe Glu Leu Asn Tyr Gln Thr Lys Asp Asn Asp Phe Pro
        355                 360                 365

Asn Asn Ile Ser Cys Ser Asn Phe Phe Met Phe Cys Leu Phe Pro Val
    370                 375                 380

Leu Val Tyr Gln Ile Asn Tyr Pro Arg Thr Ser Arg Ile Arg Trp Arg
385                 390                 395                 400

Tyr Val Leu Glu Lys Val Cys Ala Ile Ile Gly Thr Ile Phe Leu Met
                405                 410                 415

Met Val Thr Ala Gln Phe Phe Met His Pro Val Ala Met Arg Cys Ile
            420                 425                 430

Gln Phe His Asn Thr Pro Thr Phe Gly Gly Trp Ile Pro Ala Thr Gln
        435                 440                 445

Glu Trp Phe His Leu Leu Phe Asp Met Ile Pro Gly Phe Thr Val Leu
    450                 455                 460

Tyr Met Leu Thr Phe Tyr Met Ile Trp Asp Ala Leu Leu Asn Cys Val
465                 470                 475                 480

Ala Glu Leu Thr Arg Phe Ala Asp Arg Tyr Phe Tyr Gly Asp Trp Trp
                485                 490                 495

Asn Cys Val Ser Phe Glu Glu Phe Ser Arg Ile Trp Asn Val Pro Val
            500                 505                 510

His Lys Phe Leu Leu Arg His Val Tyr His Ser Ser Met Gly Ala Leu
        515                 520                 525

His Leu Ser Lys Ser Gln Ala Thr Leu Phe Thr Phe Phe Leu Ser Ala
    530                 535                 540

Val Phe His Glu Met Ala Met Phe Ala Ile Phe Arg Arg Val Arg Gly
545                 550                 555                 560

Tyr Leu Phe Met Phe Gln Leu Ser Gln Phe Val Trp Thr Ala Leu Ser
                565                 570                 575

Asn Thr Lys Phe Leu Arg Ala Arg Pro Gln Leu Ser Asn Val Val Phe
            580                 585                 590

Ser Phe Gly Val Cys Ser Gly Pro Ser Ile Ile Met Thr Leu Tyr Leu
        595                 600                 605

Thr Leu
    610

<210> SEQ ID NO 13
<211> LENGTH: 1833
<212> TYPE: DNA
<213> ORGANISM: Saccharomyces cerevisiae

<400> SEQUENCE: 13

```
atgacggaga ctaaggattt gttgcaagac gaagagtttc ttaagatccg cagactcaat    60
tccgcagaag ccaacaaacg gcattcggtc acgtacgata cgtgatcct gccacaggag    120
tccatggagg tttcgccacg gtcgtctacc acgtcgctgg tggagccagt ggagtcgact   180
gaaggagtgg agtcgactga ggcggaacgt gtggcaggga agcaggagca ggaggaggag   240
taccctgtgg acgcccacat gcaaaagtac ctttcacacc tgaagagcaa gtctcggtcg   300
aggttccacc gaaaggatgc tagcaagtat gtgtcgtttt tggggacgt gagttttgat    360
cctcgcccca cgctcctgga cagcgccatc aacgtgccct ccagacgac tttcaaaggt    420
ccggtgctgg agaaacagct caaaaattta cagttgacaa agaccaagac caaggccacg   480
gtgaagacta cggtgaagac tacggagaaa acggacaagg cagatgcccc cccaggagaa   540
aaactggagt cgaactttc agggatctac gtgttcgcat ggatgttctt gggctggata    600
gccatcaggt gctgcacaga ttactatgcg tcgtacggca gtgcatggaa taagctggaa   660
atcgtgcagt acatgacaac ggacttgttc acgatcgcaa tgttggactt ggcaatgttc   720
ctgtgcactt tcttcgtggt tttcgtgcac tggctggtga aaaagcggat catcaactgg   780
aagtggactg ggttcgttgc agtgagcatc ttcgagttgg cttcatccc cgtgacgttc    840
cccatttacg tctactactt tgatttcaac tgggtcacga aatcttcct gttcctgcac    900
tccgtggtgt ttgttatgaa gagccactcg tttgccttt acaacgggta tctttgggac    960
ataaagcagg aactcgagta ctcttccaaa cagttgcaaa aatacaagga atctttgtcc   1020
ccagagaccc gcgagattct gcaaaaaagt tgcgactttt gccttttcga attgaactac   1080
cagaccaagg ataacgactt ccccaacaac atcagttgca gcaatttctt catgttctgt   1140
ttgttccccg tcctcgtgta ccagatcaac tacccaagaa cgtcgcgcat cagatggagg   1200
tatgtgttgg agaaggtgtg cgccatcatt ggcaccatct tcctcatgat ggtcacggca   1260
cagttcttca tgcacccggt ggccatgcgc tgtatccagt tccacaacac gcccaccttc   1320
ggcggctgga tccccgccac gcaagagtgg ttccacctgc tcttcgacat gattccgggc   1380
ttcactgttc tgtacatgct cacgtttttac atgatatggg acgctttatt gaattgcgtg   1440
gcggagttga ccaggtttgc ggacagatat ttctacggcg actggtggaa ttgcgtttcg   1500
tttgaagagt ttagcagaat ctggaacgtc cccgttcaca aattttact aagacacgtg   1560
taccacagct ccatgggcgc attgcatttg agcaagagcc aagctacatt atttactttt   1620
ttcttgagtg ccgtgttcca cgaaatggcc atgttcgcca ttttcagaag ggttagagga   1680
tatctgttca tgttccaact gtcgcagttt gtgtggactg ctttgagcaa caccaagttt   1740
ctacgggcaa gaccgcagtt gtccaacgtt gtcttttcgt tggtgtctg ttcagggccc   1800
agtatcatta tgacgttgta cctgaccta tga                                 1833
```

<210> SEQ ID NO 14
<211> LENGTH: 241
<212> TYPE: PRT
<213> ORGANISM: Ustilago maydis

<400> SEQUENCE: 14

Met Ala Ser His Arg Pro Arg Ser Asn Lys Ala Asn Gly Ala Ser
1               5                   10                  15

Thr Ser Pro Lys Arg Ser Trp Ile Ile Val Ser Ala Ala Leu Val Gly
                20                  25                  30

Phe Cys Ala Leu Ile Ala Ala Leu Asp Ser Ile Arg Ser Ser Phe Tyr
            35                  40                  45

```
Ile Phe Asp His Lys Ala Ile Tyr Lys Ile Ala Ser Thr Ala Val Ala
 50                  55                  60

Asn His Pro Gly Asn Ala Thr Ala Ile Phe Asp Asp Val Leu Asp Asn
 65                  70                  75                  80

Leu Arg Ala Asp Pro Lys Leu Ala Pro Tyr Ile Asn Lys Asn His Phe
                 85                  90                  95

Ser Asp Glu Ser Glu Trp Met Phe Asn Asn Ala Gly Gly Ala Met Gly
            100                 105                 110

Ser Met Phe Ile Ile His Ala Ser Val Thr Glu Tyr Leu Ile Phe Phe
            115                 120                 125

Gly Thr Pro Val Gly Thr Glu Gly His Thr Gly Arg His Thr Ala Asp
            130                 135                 140

Asp Tyr Phe Asn Ile Leu Thr Gly Asn Gln Tyr Ala Phe Pro Ala Gly
145                 150                 155                 160

Ala Leu Lys Ala Glu His Tyr Pro Ala Gly Ser Val His His Leu Arg
                165                 170                 175

Arg Gly Thr Val Lys Gln Tyr Met Met Pro Glu Asp Gly Cys Trp Ala
            180                 185                 190

Leu Glu Leu Ala Gln Gly Trp Ile Pro Pro Met Leu Pro Phe Gly Leu
            195                 200                 205

Ala Asp Val Leu Ser Ser Thr Leu Asp Leu Pro Thr Phe Gly Ile Thr
210                 215                 220

Val Trp Ile Thr Ala Arg Glu Met Val Gly Asn Leu Leu Ile Gly Lys
225                 230                 235                 240

Phe

<210> SEQ ID NO 15
<211> LENGTH: 726
<212> TYPE: DNA
<213> ORGANISM: Ustilago maydis

<400> SEQUENCE: 15
atggcatcgc atagaccacg cagcaacaag gctgccaatg gtgcttcgac ttcacccaaa    60
cgcagctgga taattgtctc agctgcgctc gttggcttct gcgctctcat cgccgctctc   120
gattcgatcc gatccagctt ctacatcttt gaccacaagg caatctacaa gatcgcatcg   180
actgcggtcg ccaaccatcc aggcaatgcg acggccatct tgatgatgt cctcgacaac    240 cttcgtgccg accccaagct cgcgccttac atcaacaaga tcatttcag cgacgagtca    300 gaatggatgt tcaacaatgc cggtggtgct atgggtagca tgttcatcat tcatgcttcc   360
gtcaccgagt acctgatctt ctttggcact cccgtcggaa ccgagggtca cactggtcgt   420
cacacagccg atgactactt caacatcctt accggtaacc aatacgcttt ccagctggt    480 gcgctcaagg cggagcacta ccctgccgga tcagtgcacc atcttcgccg cggaacggtc   540
aagcagtaca tgatgcctga agacggctgc tgggcgctcg agcttgctca gggctggatc   600
ccacccatgc ttcccttttgg tctcgccgat gtgctcagct cgacgctcga cctgcccacc   660
tttggtatca ctgtctggat cactgcacga gaaatggttg gcaatctgct catcggcaag   720
ttttga                                                              726

<210> SEQ ID NO 16
<211> LENGTH: 25
<212> TYPE: DNA
<213> ORGANISM: Artificial Sequence
<220> FEATURE:
```

<223> OTHER INFORMATION: primer

<400> SEQUENCE: 16
tgttctgtac atgctcacgt tttac                                          25

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
cacacggtct cacaagacaa cgttggacaa ctgc                                34

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18
cacacggtct caatcaaacg aaaagacaac gttggac                             37

<210> SEQ ID NO 19
<211> LENGTH: 66
<212> TYPE: DNA
<213> ORGANISM: Artificial Sequence
<220> FEATURE:
<223> OTHER INFORMATION: primer

<400> SEQUENCE: 19
cttgtcgttt ggtgtctgtt cagggcccag tatcattatg acgttgtacc tgaccttatg    60
actgca                                                               66

<210> SEQ ID NO 20
<211> LENGTH: 58
<212> TYPE: DNA
<213> ORGANISM: Artificial Sequence
<220> FEATURE:
<223> OTHER INFORMATION: primer

<400> SEQUENCE: 20
gtcataaggt caggtacaac gtcataatga tactgggccc tgaacagaca ccaaacga      58

<210> SEQ ID NO 21
<211> LENGTH: 57
<212> TYPE: DNA
<213> ORGANISM: Artificial Sequence
<220> FEATURE:
<223> OTHER INFORMATION: primer

<400> SEQUENCE: 21
tgatgtctgt tcagggccca gtatcattat gacgttgtac ctgaccttat gactgca       57

<210> SEQ ID NO 22
<211> LENGTH: 49
<212> TYPE: DNA

```
<213> ORGANISM: Artificial Sequence
<220> FEATURE:
<223> OTHER INFORMATION: primer

<400> SEQUENCE: 22
gtcataaggt caggtacaac gtcataatga tactgggccc tgaacagac              49
```